US00PP32230P2

(12) United States Plant Patent
Kleinwee

(10) Patent No.: US PP32,230 P2
(45) Date of Patent: Sep. 22, 2020

(54) ***PETUNIA* PLANT NAMED 'PEHY0040'**

(50) Latin Name: *Petunia hybrida*
Varietal Denomination: PEHY0040

(71) Applicant: SYNGENTA CROP PROTECTION AG, Basel (CH)

(72) Inventor: Theodorus Cornelis Maria van Kleinwee, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/501,528

(22) Filed: Apr. 24, 2019

(51) Int. Cl.
*A01H 5/02* (2018.01)
*A01H 6/82* (2018.01)

(52) U.S. Cl.
USPC ..... Plt./356.15

(58) Field of Classification Search
USPC ..... Plt./356.1, 356.15
See application file for complete search history.

*Primary Examiner* — Susan McCormick Ewoldt
(74) *Attorney, Agent, or Firm* — Dale Skalla

(57) ABSTRACT

A new *Petunia* plant named 'PEHY0040' particularly distinguished by its small sized, white flowers, medium to late flowering and a trailing plant habit.

1 Drawing Sheet

Latin name of the genus and species of the plant claimed: *Petunia hybrida.*

Varietal denomination: 'PEHY0040'.

BACKGROUND OF THE NEW PLANT

The present invention comprises a new *Petunia*, botanically known as *Petunia hybrida*, and hereinafter referred to by the variety name 'PEHY0040'.

'PEHY0040' is a product of a planned breeding program. The new cultivar has small sized, white flowers, medium to late flowering and a trailing plant habit.

'PEHY0040' originated from a hybridization made in October 2013 in a controlled breeding environment in Enkhuizen, The Netherlands. The female parent was the proprietary line 'N3612-2' (not patented). Compared to 'PEHY0040', it has a comparable plant habit, a bit more vigor, is earlier, and has a deep salmon flower color.

The male parent of 'PEHY0040' was the unpatented proprietary line 'N1495-9', a plant with comparable plant habit, later flowering, less branching and a rose flower color.

The resulting seeds were sown in January 2014. 'PEHY0040' was selected as one flowering plant within the progeny of the stated cross in May 2014 in a controlled environment in Enkhuizen, The Netherlands.

The first act of asexual reproduction of 'PEHY0040' was accomplished when vegetative cuttings were propagated from the initial selection in June 2014 in a controlled environment in Angers, France.

BRIEF SUMMARY OF INVENTION

Horticultural examination of plants grown from cuttings of the plant initiated in June 2014 and continuing thereafter, has demonstrated that the combination of characteristics as herein disclosed for 'PEHY0040' are firmly fixed and are retained through successive generations of asexual reproduction.

'PEHY0040' has not been observed under all possible environmental conditions. The phenotype may vary significantly with variations in environment such as temperature, light intensity, and day length.

A Plant Breeder's Right for this cultivar has not yet been applied for. 'PEHY0040' has not been made publicly available prior to the effective filing date of this application, notwithstanding any disclosure that may have been made less than one year prior to the effective filing date of this application by the inventor or another who obtained 'PEHY0040' directly from the inventor.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

Figure 1:
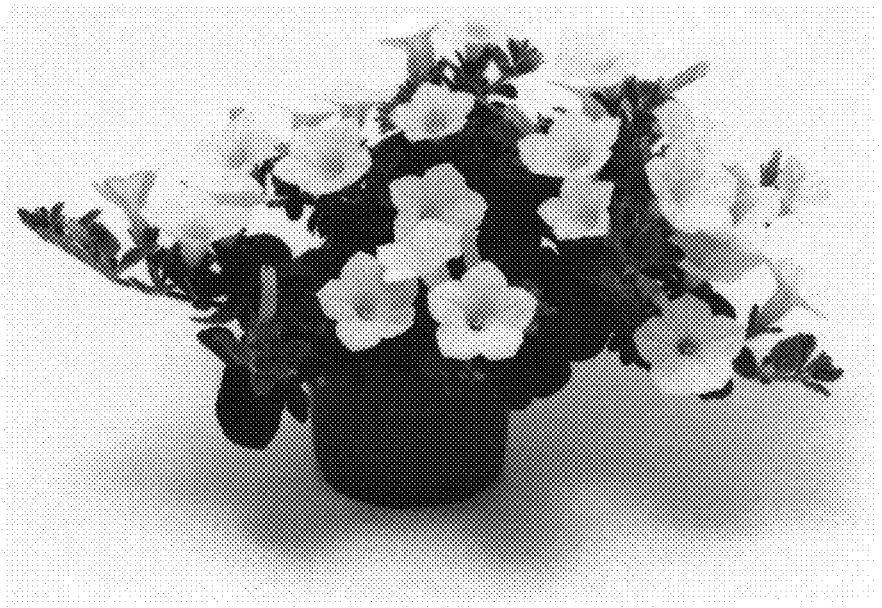
Figure 2:
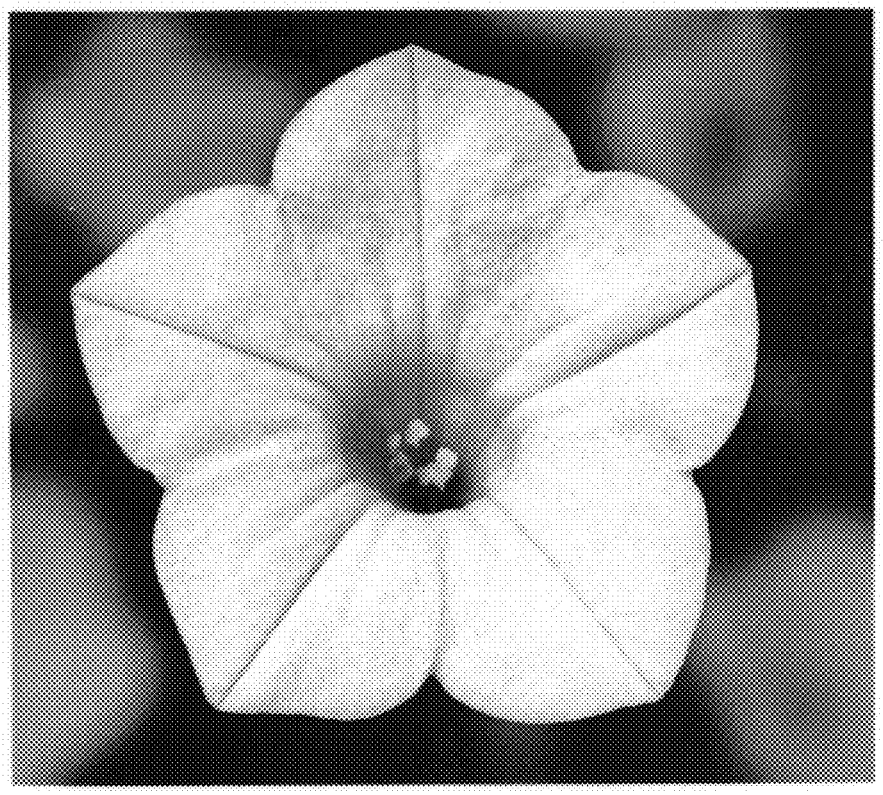

The accompanying photographic drawings show typical flower and foliage characteristics of 'PEHY0040' with colors being as true as possible with an illustration of this type. The photographic drawings show in FIG. 1 a flowering plant of the new variety and in FIG. 2 a close-up of the flower.

DETAILED BOTANICAL DESCRIPTION

The aforementioned photographs were taken in April 2018 from plants growing indoor in 12 cm pots in Andijk, The Netherlands. These plants were approximately 11 weeks of age.

The plant descriptions and measurements were taken in September 2018 in Andijk, The Netherlands on approximately 20 week old plants that were growing in containers.

Color references are made to The Royal Horticultural Society Colour Chart (R.H.S.) 2001.

TABLE 1

DIFFERENCES BETWEEN THE NEW VARIETY 'PEHY0040' AND A MOST SIMILAR VARIETY

| | 'PEHY0040' | 'PEHY0028' (Not patented) |
|---|---|---|
| Flower shape: | Flat | Cup shaped |
| Flower color: | Pure white | White, some greenish shade in throat |
| Earliness: | Medium to late | Late |

Plant:
- *Form, growth and habit.*—Semi-trailing plant habit.
- *Plant height.*—22 cm.
- *Plant height (inflorescence included).*—25 cm.
- *Plant diameter (width).*—Approximately 40 cm.

Roots:
- *Number of days to initiate and produce roots.*—16 days at about 22° C.
- *Type.*—Fine, fibrous, free branching.
- *Color.*—RHS N158D.

Foliage:
- *Arrangement.*—Alternate, simple; sometimes opposite, decussate.
- *Immature leaf, color upper surface.*—RHS 147A.
- *Immature leaf, color lower surface.*—RHS 147B.
- *Mature leaf, color upper surface.*—RHS 147A.
- *Mature leaf, color lower surface.*—RHS 147B.
- *Length.*—1.6-2.5 cm.
- *Width.*—1.1-2.0 cm.
- *Shape.*—Ovate.
- *Base shape.*—Shortly attenuate.
- *Apex shape.*—Rounded to acute.
- *Margin.*—Entire.
- *Texture, upper surface.*—Densely covered with short hairs.
- *Lower surface.*—Densely covered with short hairs.
- *Color of veins, upper surface.*—RHS 144C.
- *Color of veins, lower surface.*—RHS 146B.
- *Petiole color.*—RHS 146B.
- *Length.*—0.3 cm.
- *Diameter.*—0.2 cm.
- *Petiole texture.*—Densely covered with short hairs.

Stem:
- *Quantity of main branches per plant.*—4-5.
- *Color of stem.*—RHS 146B.
- *Length of stem.*—24 cm.
- *Diameter.*—0.4 cm.
- *Length of internodes.*—2-3 cm.
- *Texture.*—Dense, mostly glandular short hairs.
- *Color of pedicel.*—RHS 146B.
- *Length of pedicel.*—1.6 cm.
- *Diameter of pedicel.*—0.2 cm.
- *Texture of pedicel.*—Densely covered with short hairs.

Inflorescence:
- *Type.*—Flowers solitary in upper leaf axis.
- *Floret type.*—Funnel-shaped; 5 lobed petals; fused at base.
- *Blooming habit.*—Medium to late flowering in greenhouse, flowering throughout the summer. months.
- *Quantity of inflorescences per plant.*—Approximately 45.
- *Lastingness of individual blooms on the plant.*—About 7 days.
- *Fragrance.*—Medium strong smell.

Bud (just when opening):
- *Color.*—RHS 149D.
- *Length.*—2.0 cm.
- *Width.*—0.4 cm.
- *Shape.*—Oblong.

Immature inflorescence:
- *Flower horizontal diameter.*—2.8 cm.
- *Color petals, upper surface.*—Whiter than RHS 155A with veins RHS 145B.
- *Color petals, lower surface.*—Whiter than RHS 155A with veins RHS 145A.

Mature flower:
- *Flower horizontal diameter.*—4 cm.
- *Flower height (vertical).*—3 cm.
- *Color upper surface.*—Whiter than RHS 155A.
- *Color lower surface.*—Whiter than RHS 155A with veins RHS 145B.
- *Conspicuousness of veins.*—Medium.
- *Apex shape.*—Rounded to slightly acuminate.
- *Margin.*—Entire.
- *Waviness of margin.*—Hardly any waviness.
- *Petal lobation.*—Little.
- *Petal texture, upper surface.*—Smooth.
- *Petal texture, lower surface.*—Some glandular hairs, more dense on veins.
- *Corolla tube color outside.*—RHS 145D with stripes RHS 145B.
- *Corolla tube color inside.*—RHS 145C with longitudinal stripes RHS 145B.
- *Conspicuousness of veins in tube.*—Rather strong.
- *Corolla tube length.*—1.8 cm.
- *Corolla tube texture, outside.*—Rather dense and short glandular hairs.
- *Corolla tube texture, inside.*—Glabrous.

Calyx:
- *Color of sepal, upper surface.*—RHS 147A.
- *Color of sepal, lower surface.*—RHS 147B.
- *Length.*—1.3 cm.
- *Width.*—0.4-0.7 cm.
- *Shape.*—Oblanceolate.
- *Apex shape.*—Rounded.
- *Base.*—Fused.
- *Margins.*—Entire.
- *Texture, upper surface.*—Densely covered with short glandular hairs.
- *Lower surface.*—Densely covered with short glandular hairs.

Reproductive organs:
- *Pistil.*—1.
- *Length.*—1.9 cm.
- *Style color.*—RHS 144C.
- *Style length.*—1.4 cm.
- *Stigma color.*—RHS 144B.
- *Stamens.*—
- *Quantity per flower.*—5.
- *Color of filaments.*—RHS 145D.
- *Length filaments.*—1.5 cm.
- *Anther color.*—RHS 162A.
- *Anther length.*—0.2 cm.
- *Anther shape.*—Elliptical.
- *Color of pollen.*—RHS 196C.
- *Pollen amount.*—Sparse.
- *Fertility/seed set.*—Has not been observed on this hybrid.
- *Disease/pest resistance.*—Has not been observed on this hybrid.

What is claimed is:

1. A new and distinct variety of *Petunia* plant named 'PEHY0040' substantially as illustrated and described herein.

* * * * *